United States Patent
Potts et al.

(10) Patent No.: US 6,867,344 B2
(45) Date of Patent: Mar. 15, 2005

(54) ABSORBENT ARTICLE WITH FLUID TREATMENT AGENT

(75) Inventors: David Charles Potts, Dunwoody, GA (US); Brian Eric Lin, Alpharetta, GA (US); Cheryl Ann Mocadlo, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 214 days.

(21) Appl. No.: 10/034,855

(22) Filed: Dec. 28, 2001

(65) Prior Publication Data

US 2003/0124936 A1 Jul. 3, 2003

Related U.S. Application Data (63) Continuation-in-part of application No. 10/035,701, filed on Nov. 9, 2001, now Pat. No. 6,812,169, which is a continuation of application No. 09/183,170, filed on Oct. 30, 1998, now Pat. No. 6,350,711.

(51) Int. Cl.[7] ................................. A61F 13/15
(52) U.S. Cl. ................ 604/367; 442/121; 442/123; 442/327; 442/381; 442/417; 502/400; 502/405; 502/526
(58) Field of Search ................. 442/121, 123, 442/327, 381, 417; 502/400, 405, 526, 401, 402, 404; 604/367

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |

(List continued on next page.)

FOREIGN PATENT DOCUMENTS

| | | |
|---|---|---|
| EP | 0 009 977 A1 | 4/1980 |
| EP | 019 371 | 11/1980 |
| EP | 0 510 619 A1 | 10/1992 |
| EP | 0 793 971 A1 | 9/1997 |
| EP | 793 971 | 9/1997 |
| WO | 93/21879 | 11/1993 |
| WO | 95/19191 | 7/1995 |
| WO | 96/40300 | 12/1996 |
| WO | WO 97/24378 | 7/1997 |
| WO | WO 98/09662 | 3/1998 |
| WO | 98/10134 | 3/1998 |
| WO | 99/04831 | 2/1999 |
| WO | WO 99/12505 | 3/1999 |
| WO | 99/32706 | 7/1999 |
| WO | 99/61079 | 12/1999 |
| WO | 00/25835 | 5/2000 |
| WO | 00/51655 | 9/2000 |
| WO | WO 01/00156 | 1/2001 |
| WO | 01/45615 | 6/2001 |
| WO | 01/91684 A2 | 12/2001 |
| WO | WO 02/45762 | 6/2002 |

*Primary Examiner*—Ula Ruddock
*Assistant Examiner*—Jennifer Boyd
(74) *Attorney, Agent, or Firm*—Pauley Petersen & Erickson (57) ABSTRACT

A personal care absorbent article, such as a sanitary pad or napkin, wound dressing, and the like having one or more layers of absorbent material treated with a red blood cell lysing agent and a gelling agent. The effect of combining a lysing agent that thins menses or other blood-containing bodily fluids with a gelling agent that thickens menses or other blood-containing bodily fluids is enhanced agglomeration and increased viscosity of the blood-containing bodily fluids that come in contact with the treated material.

25 Claims, 3 Drawing Sheets

U.S. PATENT DOCUMENTS

| | | |
|---|---|---|
| 3,802,817 A | 4/1974 | Matsuki et al. |
| 3,849,241 A | 11/1974 | Butin et al. |
| 4,167,464 A | 9/1979 | George |
| 4,190,563 A | 2/1980 | Bosley et al. |
| 4,340,563 A | 7/1982 | Appel et al. |
| 4,358,394 A | 11/1982 | Crews et al. |
| 4,381,784 A | 5/1983 | Aberson et al. |
| 4,435,172 A | 3/1984 | Gross |
| 4,462,989 A | 7/1984 | Cerami |
| 4,488,928 A | 12/1984 | Ali Khan et al. |
| 4,565,663 A | 1/1986 | Errede et al. |
| 4,614,787 A | 9/1986 | Szycher et al. |
| 4,693,713 A | 9/1987 | Chmelier et al. |
| 5,082,723 A | 1/1992 | Gross et al. |
| 5,108,827 A | 4/1992 | Gessner |
| 5,190,657 A | 3/1993 | Heagle et al. |
| 5,281,208 A | 1/1994 | Thompson et al. |
| 5,336,552 A | 8/1994 | Strack et al. |
| 5,382,400 A | 1/1995 | Pike et al. |
| 5,460,622 A | 10/1995 | Dragoo et al. |
| 5,486,167 A | 1/1996 | Dragoo et al. |
| 5,529,933 A | 6/1996 | Young et al. |
| 5,558,834 A | 9/1996 | Chu et al. |
| 5,700,254 A | 12/1997 | McDowall et al. |
| 5,759,844 A | 6/1998 | Hiraki et al. |
| 5,762,871 A | 6/1998 | Neyer |
| 5,797,891 A | 8/1998 | Wiersma |
| 5,998,032 A | 12/1999 | Hansen et al. |
| 6,017,832 A | 1/2000 | Yahiaoui et al. |
| 6,060,636 A | 5/2000 | Yahiaoui et al. |
| 6,177,367 B1 | 1/2001 | Mathis |
| 6,231,557 B1 | 5/2001 | Krautkramer et al. |
| 6,296,936 B1 | 10/2001 | Yahiaoui et al. |
| 2001/0018068 A1 | 8/2001 | Lorenzi et al. |
| 2002/0040210 A1 | 4/2002 | Luccio et al. |

ABSORBENT ARTICLE WITH FLUID TREATMENT AGENT

CROSS REFERENCE TO RELATED APPLICATION

This application is a continuation-in-part of U.S. patent application Ser. No. 10/035,701 filled 9 Nov. 2001 now U.S. Pat. No. 6,812,169 by Express Mail No. EL859246575US, which is a continuation of U.S. patent Application Ser. No. 09/183,170 filed 30 Oct. 1998 now U.S. Pat. No. 6,350,711.

BACKGROUND OF THE INVENTION

This invention relates to a treatment for absorbent material that improves the materials' ability to absorb various blood-containing bodily fluids.

A wide variety of disposable absorbent articles for collecting bodily fluids are known in the art. Commercial absorbent articles include diapers, sanitary napkins, training pants, and incontinent care pads, wound dressings, and the like. Disposable products of this type include some functional elements for receiving, absorbing, and retaining fluids. Typically, such absorbent articles have an absorbent core containing cellulosic fibers, for example, wood pulp fluff, polymeric fibers, for example polypropylene or polyethylene, particles of highly absorbent materials, for example, superabsorbents, and an admixture of cellulosic fibers, superabsorbents and/or polymeric fibers. Typically, such articles include a fluid-permeable cover sheet or liner which typically faces the body of the user, an absorbent core or containment layer, and a fluid-impermeable backsheet.

Cover sheet materials are utilized for the transport of bodily fluids into the absorbent core of personal care absorbent articles and, thus, materials used for cover sheet applications must manage distinctly different body excretions, depending upon the application and the product type. Some products must manage fluids, such as urine, while others must manage proteinaceous and viscoelastic fluids, such as menstrual discharge and fecal matter. The management of viscoelastic menstrual discharge by feminine care products such as sanitary pads and napkins is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the absorbent core.

There are several factors which influence the flow of liquids in fibrous structures including the geometry of the pore structure in the fabrics, the nature of the solid surface (surface energy, surface charge, etc.), the geometry of the solid surface (surface roughness, grooves, etc.), the chemical/physical treatment of the solid surface, and the chemical nature of the fluid. One problem associated with absorbent articles intended for use in handling fluids comprising blood components such as feminine care products and wound dressings is the tendency of red blood cells to block the pores of the materials used for absorption of fluids in such products. Typical of such porous materials are nonwoven or fibrous web materials. The blockage of the pores of the nonwoven or fibrous web materials by the red blood cells results in a reduction in the fluid intake and the wicking capabilities of such products. In addition, in the case of feminine care products such as sanitary pads and napkins, the blockage of pores of nonwoven materials used therein by red blood cells results in increased staining. In the case of feminine care products comprising superabsorbents, the red blood cells attach themselves to the superabsorbents, resulting in blockage of the superabsorbents and a significant reduction in fluid uptake.

In the case of feminine care products such as sanitary pads and napkins, women have come to expect a high level of performance in terms of comfort and fit, retention of fluid, and minimal staining. Of utmost importance, leakage of fluid from the pad onto undergarments is regarded as totally unacceptable.

Improving the performance of feminine care products continues to be a formidable undertaking, although numerous improvements have been made in both their materials and structures. However, solutions addressing the issues arising from the presence of red blood cells in blood or menses in feminine care products, as well as other absorbent materials for handling blood-containing fluids, have not been satisfactorily implemented. It is apparent that a system which effectively handles red blood cells in a manner which addresses the issues set forth hereinabove will not only improve the distribution of incoming fluids by the absorbent material, but will also reduce the tendency toward premature failures of these absorbent articles.

Methods for separating or removing red blood cells from blood-containing fluids generally fall into two categories, agglutination (agglomeration) in which the red blood cells agglomerate, thereby enabling them to be more readily separated from the remaining fluid component, for example, by filtration; and lysing in which the membranes of the red blood cells are disrupted, resulting in a breaking down or breaking apart of the red blood cells. Agglomeration is known to occur, for example, in the presence of certain antibodies. The ability of gelling agents to increase the viscoelastic properties of biological menses simulant has previously been demonstrated. Furthermore, the ability of red blood cell lysing agents to break down red blood cells in biological menses simulant is known. However, we are unaware of any absorbent material treatments that combine a gelling agent with a red blood cell lysing agent.

There is a need or desire for an absorbent system that can effectively handle red blood cells.

SUMMARY OF THE INVENTION

In response to the discussed difficulties and problems encountered in the prior art, a new treatment for absorbent materials that allows the absorbent materials to effectively handle red blood cells has been discovered.

The present invention is directed to a composition for treating absorbent material which allows the absorbent material to effectively handle red blood cells, thereby improving the material's ability to absorb a blood-containing fluid. The composition includes a gelling agent, such as a menses gelling agent, and a red blood cell lysing agent. The gelling agent causes the red blood cells in the blood-containing fluid to agglomerate, thereby enabling them to be physically separated from the blood-containing fluid, leaving a fluid that is easier to absorb and less strongly colored. Conversely, the lysing agent breaks down the structure of the red blood cells. Used in conjunction with one another, a synergy develops in which the red blood cell lysing agent enhances the gelling effects of the gelling agent such that the gelling agent works better and more efficiently in combination with the lysing agent than on its own, as exhibited by higher viscosity results when mixed with menses simulant. For maximum performance, however, the gelling agent and the lysing agent are applied separately and are not integrated together into components.

In one embodiment of the invention, the gelling agent and the red blood cell lysing agent are applied to an absorbent material. The gelling agent and lysing agent can be applied to separate product components, or can be applied to the same component. For example, the gelling agent and the lysing agent can be applied to different layers of material within a single laminate. Furthermore, the lysing agent can be applied to a central region or insult area of one layer while the gelling agent can be applied to a peripheral region of the same layer or another layer.

In another embodiment, the gelling agent and the red blood cell lysing agent are applied to components within an absorbent article, such as a catamenial article. More particularly, the lysing agent can be applied to a liner or an intake layer adjacent the liner, while the gelling agent can be applied to a containment layer, such as an absorbent core.

One of the benefits of this invention derives from the fact that the red blood cells of a blood-containing fluid, having come into contact with the gelling agent and the lysing agent, are no longer able to block the flow of fluids into any superabsorbents that may be present in the absorbent material.

With the foregoing in mind, particular embodiments of the invention provide absorbent materials and absorbent articles that can effectively handle red blood cells.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS DEFINITIONS

As used herein, the term "nonwoven web" or "fibrous web" refers to any material comprising fibrous or fiber-like elements, usually in a random arrangement, joined by bonding points which stabilize the structure, providing at least some mechanical integrity, which form at least some small pores throughout the length and width thereof between adjacent fiber-like elements. The term also includes individual filaments and strands, yarns or tows as well as foams and films that have been fibrillated, apertured or otherwise treated to impart fabric-like properties. "Nonwoven webs" or "fibrous webs" are formed by many processes such as, for example, spunbonding, meltblowing, airlaid, airformed, wetlaid, coform and bonded carded processes.

As used herein, the term "spunbonding" refers to a process in which small diameter fibers are formed by extruding molten thermoplastic materials as filaments from a plurality of fine, usually circular capillaries of a spinneret with the diameter of the extruded filaments then being rapidly reduced as, for example, described in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992, U.S. Pat. No. 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Such a process is disclosed, for example, by U.S. Pat. No. 3,849,241 to Butin. Meltblown fibers are microfibers which may be continuous or discontinuous and are generally smaller than 10 microns in average diameter.

As used herein, the term "bonded carded" or "bonded carded webs" refers to nonwoven webs formed by carding processes as are known to those skilled in the art and further described, for example, in U.S. Pat. No. 4,488,928 to Alikhan and Schmidt. Typically, carding processes involve starting with a blend of, for example, staple fibers with bonding fibers or other bonding components in a bulky batt that is combed or otherwise treated to provide a generally uniform basis weight. This web is heated or otherwise treated to activate the adhesive component, resulting in an integrated, usually lofty nonwoven material.

As used herein, the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives are generally present in an amount less than about 5 weight percent and more typically about 2 weight percent.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across a cross-section of the conjugate fibers and extend continuously along the length of the conjugate fibers. The configuration of such a conjugate fiber may be, for example, a sheath/core arrangement in which one polymer is surrounded by another, or may be a side-by-side arrangement, or an "islands-in-the-sea" arrangement. Conjugate fibers are taught, for example, by U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75, or any other desired ratios.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, syndiotactic, and random symmetries.

As used herein, the term "absorbent material" refers to any material having fluid absorption properties.

As used herein, the term "personal care absorbent articles" refers to diapers, training pants, absorbent underpants, adult incontinence products, wound dressings, sanitary wipes and feminine hygiene products such as sanitary napkins, pads, and tampons.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "stain" refers to fluid, wet or dry, which is present on the top surface, in, or on the bottom surface of a cover material or liner of a personal care absorbent article.

As used herein, the term "gradient porosity" refers to a porous system in which the average pore size in the system decreases (or increases) from one side of the system to the opposite side of the system. In the case of personal care absorbent articles employing porosity gradient nonwoven web materials in accordance with this invention, average pore sizes decrease from the side of the nonwoven web material disposed towards the liner or cover of the absorbent article in the direction of the liquid impervious backsheet.

"Low viscoelastic simulant" or "menses simulant" is another material which simulates the viscoelastic and other properties of menses. To prepare the fluid, blood, such as defibrinated swine blood, is separated by centrifuge at 3000 rpm for 30 minutes, although other methods or speeds and times may be used if effective. The plasma is separated and stored separately, the buffy coat removed and discarded, and the packed red blood cells stored separately as well. Eggs, such as jumbo chicken eggs, are separated, the yoke and chalazae discarded, and the egg white retained. The egg white is separated into thick and thin portions by straining the white through a 1000 micron nylon mesh for about three minutes, and the thinner portion discarded. Alternative mesh sizes may be used, and the time or method may be varied provided the viscosity is at least that required. The thick portion of egg white which was retained on the mesh is collected and 80 ml is mixed with 60 ml of swine plasma. The material is then sheared by any appropriate method to achieve a homogeneous solution with a viscosity of about 7–15 cps at 1 sec$^{-1}$ at 22 degrees Celsius. After centrifuging, 80 mL of the thick homogenized egg white, which contains ovomucin, is added to a 300 cc FENWAL Transfer Pack using a syringe. Then, 60 cc of the swine plasma is added to the transfer pack. The transfer pack is clamped, all air bubbles removed, and placed in a Stomacher lab blender in which it is blended at normal (or medium) speed for about two minutes. The transfer pack is then removed from the blender, 60 cc of swine red blood cells are added, and the contents mixed by hand kneading for about two minutes, or until the contents appear homogeneous. The final mixture has a red blood cell content of about 30 volume percent and generally is at least within the range of 28–32 volume percent for artificial menses. The amount of egg white is about 40 weight percent.

Menstrual discharges are composed of blood, vaginal or cervical secretions and endometrial tissues, also called clots. The vaginal secretions are mainly composed of mucins. The proportions of the various components of menstrual fluid vary from woman to woman and from period to period. The proportions of these components also depend upon the age of the woman, the activity of the woman and the method of birth control used by the woman. As a result, the fluid composition can vary from 30 to 70% blood, 10 to 50% cervical secretions, and 0 to 30% endometrial tissues.

There are several factors which influence the flow of liquids in fibrous structures including the geometry of the pore structure in the fabrics, the nature of the solid surface (surface energy, surface charge, etc.), the geometry of the solid surface (surface roughness, grooves, etc.), the chemical/physical treatment of the solid surface, and the chemical nature of the fluid.

This invention, in accordance with one embodiment, provides a treatment for an absorbent material suitable for use in personal care absorbent articles such as sanitary pads, napkins and tampons, wound dressings and the like, the intended purpose of which is to absorb and store blood-containing fluids. The absorbent material of this invention reduces the impact of red blood cells on fluid intake, wicking capabilities, staining, and overall fluid containment, in particular, the functionality of superabsorbent particles.

The treatment is a composition including a red blood cell lysing agent and a gelling agent. Suitably, the gelling agent is present in a concentration of between about 0.1% and about 1.0%, or between about 0.2% and about 0.9%, or between about 0.3% and about 0.8% by weight of the liquids involved, which when applied to a substrate is between about 1% and about 15%, or between about 2% and about 10%, or between about 3% and about 8% by weight of the substrate. The lysing agent is present in a concentration of between about 0.2% and about 4.0%, or between about 0.6% and about 3.5%, or between about 0.8% and about 3.0% by weight of the liquids involved, which when applied to a substrate is between about 2% and about 40%, or between about 6% and about 35%, or between about 8% and about 30% by weight of the substrate. Together, the lysing agent and the gelling agent work to increase viscosity of blood-containing fluids with which they come into contact, as demonstrated in the example below. More particularly, when combined with a biological menses stimulant, for example in a ratio of about 1:200, the composition and the menses simulant exhibit a viscosity of at least 4.0 P, or at least 4.2 P, or at least 4.4 P within 15 minutes of applying the composition to the menses simulant.

A delay in time between exposure of the menses simulant to the lysing agent and exposure of the menses simulant to the gelling agent results in even greater viscosity than exposure of the menses simulant to both the lysing agent and the gelling agent at the same time. For example, when the menses simulant is first combined with the lysing agent and 30 minutes later is then combined with the gelling agent in a ratio between the menses simulant and the composition of about 1:200, the composition and the menses simulant exhibit a viscosity of at least 4.8 P, or at least 5.0 P, or at least 5.2 P within 45 minutes of combining the menses simulant with the lysing agent.

The invention also includes an absorbent material treated with the red blood cell lysing agent and the gelling agent. The invention further includes a personal care absorbent article in which one or more components made of absorbent material are treated with the red blood cell lysing agent and the gelling agent.

A wide variety of disposable personal care absorbent articles for collecting bodily fluids, which articles typically comprise nonwoven web materials, are known in the art. Commercial absorbent articles include disposable diapers, sanitary napkins, training pants, and incontinent care pads, wound dressings, and the like. Disposable products of this type include some functional elements for receiving, absorbing, and retaining fluids. Typically, such absorbent articles have an absorbent core or containment layer containing cellulosic fibers, for example, wood pulp fluff, particles of highly absorbent materials, for example, superabsorbents, and an admixture of cellulosic fibers and superabsorbents.

Figure 1:
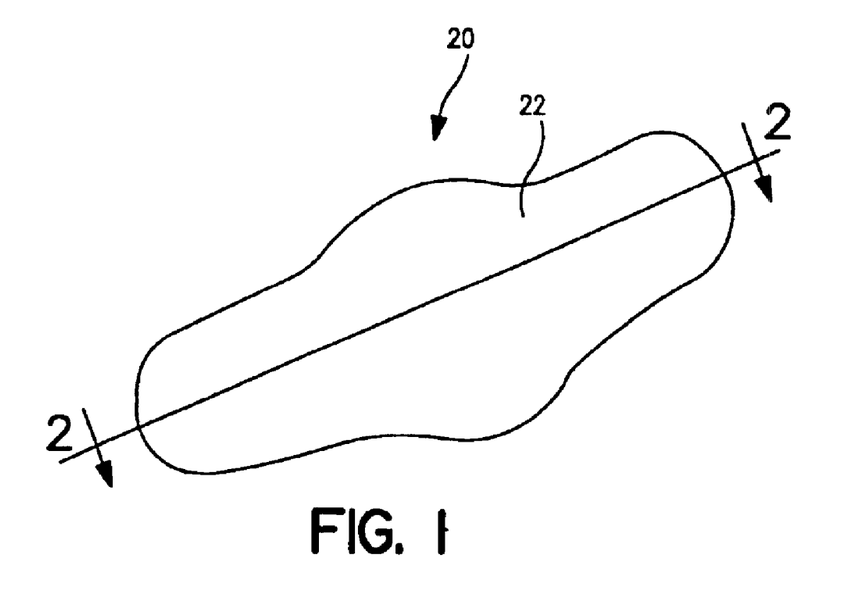
FIG. 1 is a perspective view of an absorbent article.
Figure 2:
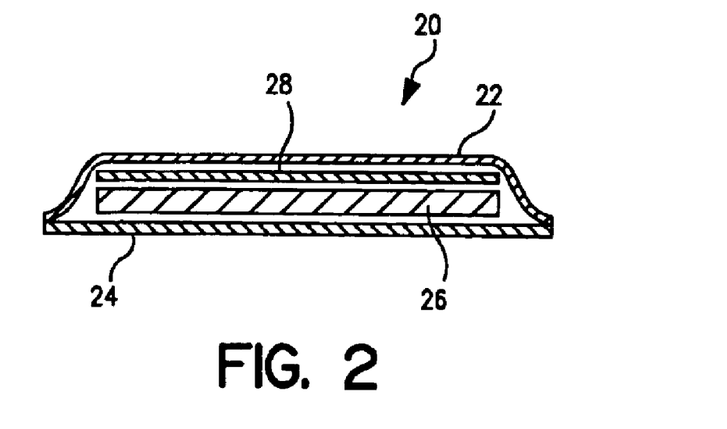
FIG. 2 is a cross-sectional view of the absorbent article of FIG. 1, taken along line 2—2.

An example of a personal care absorbent article 20 including absorbent material treated in accordance with the present invention is shown in FIG. 1. A cross-section of the absorbent article 20 is shown in FIG. 2, which exhibits the various layers of the absorbent material that makes up the absorbent article 20. More particularly, the absorbent article 20 may include a fluid-permeable liner 22 which faces the body of the user, and on an opposite surface of the absorbent article a fluid impervious baffle 24 that faces away from the wearer while the article is in use. Absorbent material within the article 20 may include the liner 22, as well as a containment layer 26 positioned between the liner 22 and the fluid impervious baffle 24. An additional absorbent material, namely an intake layer 28, may be positioned between the liner 22 and the containment layer 26 to provide added intake capability to the article.

Liner materials are utilized for the transport of bodily fluids into the containment layer of personal care absorbent articles and, thus, materials used for liner applications must manage distinctly different body excretions, depending upon the application and the product type. Some products must manage fluids, such as urine, while others must manage proteinaceous and viscoelastic fluids, such as menstrual discharge and fecal matter. The management of viscoelastic menstrual discharge by feminine care products such as sanitary pads and napkins is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the containment layer.

At least one of the layers within the absorbent material, or within the absorbent article, is treated with the red blood cell lysing agent, and at least one of the layers within the absorbent material, or within the absorbent article, is treated with the gelling agent. Suitably, blood-containing fluids first come in contact with the lysing agent before coming in contact with the gelling agent. Therefore, it is desirable for the layer with the lysing agent to be in closer contact with a wearer than the layer with the gelling agent. In one embodiment, the liner is treated with the red blood cell lysing agent and the containment layer is treated with the gelling agent. In another embodiment, the intake layer is treated with the red blood cell lysing agent and the containment layer is treated with the gelling agent.

The location of the lysing agent and the gelling agent within the absorbent material or within the absorbent article can be further optimized by applying the lysing agent to a central region of a layer of absorbent material and applying the gelling agent to a peripheral region of either the same or a different layer of absorbent material, thereby preparing a target area in the central region for the blood-containing fluid to first contact, after which the lysed fluid will most likely radiate outward toward the peripheral region where the gelling agent will agglomerate the fluid and prevent any further spread of the fluid. As used herein, the term "peripheral region" refers to a region along the periphery of a layer suitably within about 1.5 inches (3.8 cm) of an edge of the layer, desirably within about 0.5 inch (1.3 cm) of an edge of the layer. The term "central region," as used herein, refers to a region of a layer surrounded by the peripheral region.

The absorbent material in this invention may be a porous, nonwoven material which may be produced by any method known to those skilled in the art for producing nonwoven web materials. The absorbent material may be airformed, airlaid, or a bonded carded web, for example. Liner material, in particular, may include a fluid permeable polymeric film.

In accordance with one embodiment of this invention, the average pore size of the pores of the nonwoven web material is in the range of about 10 microns to about 200 microns, thereby ensuring that the individual red blood cells will be able to pass through the outermost pores of the nonwoven web material into the interior thereof while also ensuring that the agglomerated red blood cells will be unable to pass through the pores to contact superabsorbents which may be present.

In accordance with one embodiment of this invention, the absorbent material of this invention is a multilayer laminate in which absorbent material layers having different average pore sizes are layered one upon another so as produce an absorbent laminate having a porosity gradient as defined hereinabove.

Alternatively, the absorbent material may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it is then bonded by one or more of several known bonding methods. One such bonding method is powder bonding wherein a powdered adhesive is distributed through the web and then activated, usually by heating the web and adhesive with hot air or some other heat source. Another suitable bonding method is pattern bonding wherein heated calender rolls or ultrasonic bonding equipment are used to bond the fibers together, usually in localized bond pattern, though the web can be bonded across its entire surface, if so desired. Another suitable bonding method, particularly when using bicomponent staple fibers, is through-air bonding.

The absorbent material, particularly in the containment layer and/or the intake layer, may include a superabsorbent. An example of a commercially available superabsorbent polymer is FAVOR 880®, available from Stockhausen, Inc. 2401 Doyle Street Greensboro, N.C. 27406.

Gelling agents are protein cross-linking agents that gel the fluid by producing a matrix of protein and cationic polymers that is hydrated. We have found that all cationic polymers do not work equally well. Suitable ionically cross-linking gelling agents for use in the personal care articles of this invention include CELQUAT® (National Starch and Chemical Company) which is a polyquaternium cellulosic polymer, UCARE™ polymers which include cellulose with propylene oxide groups (Amercol division of Union Carbide) and chitosan (Vanson), which are mixed with a non-debonded pulp (NB416) available from Weyerhaeuser Corporation of Tacoma, Wash. Air Products Polymers and Chemicals sells other suitable binder fibers under the name AIRFLEX®. The CELQUAT® polymers appear to work the best and, thus, are preferred. These include the L-200, H-100, SC-230 and SC-240, available from National Starch and Chemical Company. In each case, a polymer of glucose is connected with β(1→4) linkages (it has been shown that α(1→4) linkages have much lower effectiveness). This is taken to mean that a relatively stiff polyglycan backbone produces increased effectiveness. It is apparent that other polyglycan structures that have reduced rotation, and are therefore stiff, would also be effective; or for that matter any polymer with reduced freedom of movement would suffice. Whatever the case may be, the stiff backbone has positive charges at intervals along the backbone. These positive charges come from ammonium ions in the case of CELQUAT®, UCARE™ and chitosan salts, but could, in principle, be produced from other substituents as well.

As a result of treatment of the absorbent material with a gelling agent, the red blood cells clump together and are "filtered" out of the menses or blood as a result of being trapped in the pores of the nonwoven web material, for example.

Suitable lysing agents for use in the absorbent materials of this invention include GLUCOPON 220, an octylpolyglycoside available from Henkel Corporation, Ambler, Pa., MASILE SF-19, an alkoxylated polysiloxane available from PPG Industries, Inc., Specialty Chemicals Division, Gurnee, Ill., nonionic surfactant LAURETH 7, an alkoxylated alcohol available from Heterene, Inc., Paterson, N.J., nonionic LAURETH 4, an alkoxylated alcohol available from Heterene, Inc., nonionic PPG 5-Laureth 5, an alkoxylated alcohol available from Henkel Corporation, amphoteric surfactant DERIPHAT 160S, an alkyl-substituted amino acid available from Henkel/Cospha, Ambler, Pa., anionic surfactant sodium laurel sulfate, an alkyl sulfate available from Henkel, amphoteric MACKAM 15-L, an alkyl substituted amino acid available from McIntyre Group, University Park, Ill., anionic MACKANATE LM-40, a sulfosuccinate available from McIntyre Group, anionic STANDOPOL SH124-3, a sulfosuccinate available from Henkel/Cospha, and anionic HAMPOSYL L-30, a sarcosinate available from Hampshire Chemical, Lexington, Mass.

In accordance with one embodiment of this invention, the red blood cell lysing agent is a saponin, a high molecular weight glycoside comprising a sugar part linked to a triterpene or steroid aglycone. A suitable saponin produced from quillaja bark is available from Sigma Chemical Company, St. Louis, Mo.

Both the gelling agent and the lysing agent may be applied to the absorbent material by any means known to those skilled in the art including dipping the absorbent material into a solution of the agent or spraying the agent directly onto the absorbent material.

EXAMPLE

A Theological test was used to demonstrate the performance of the composition of the invention. The testing was carried out using a Vilastic III capillary rheometer equipped with a 1 millimeter diameter capillary tube, available from Vilastic Scientific, located in Austin, Tex. The instrument was set up to take 30 time course measurements of a fluid's viscoelasticity in equal increments over a 15 minute time frame. These measurements were taken at a single frequency of 0.5 Hz and shear rate of 1 s$^{-1}$.

When 0.5% UCARE™ gelling agent and 0.6% GLUCOPON 220 red blood cell lysing agent were added to a biological menses stimulant, made according to the method described above and time course viscoelastic measurements were immediately taken, both the rate and degree of gelling were increased compared to the addition of UCARE™ alone.

Figure 3:
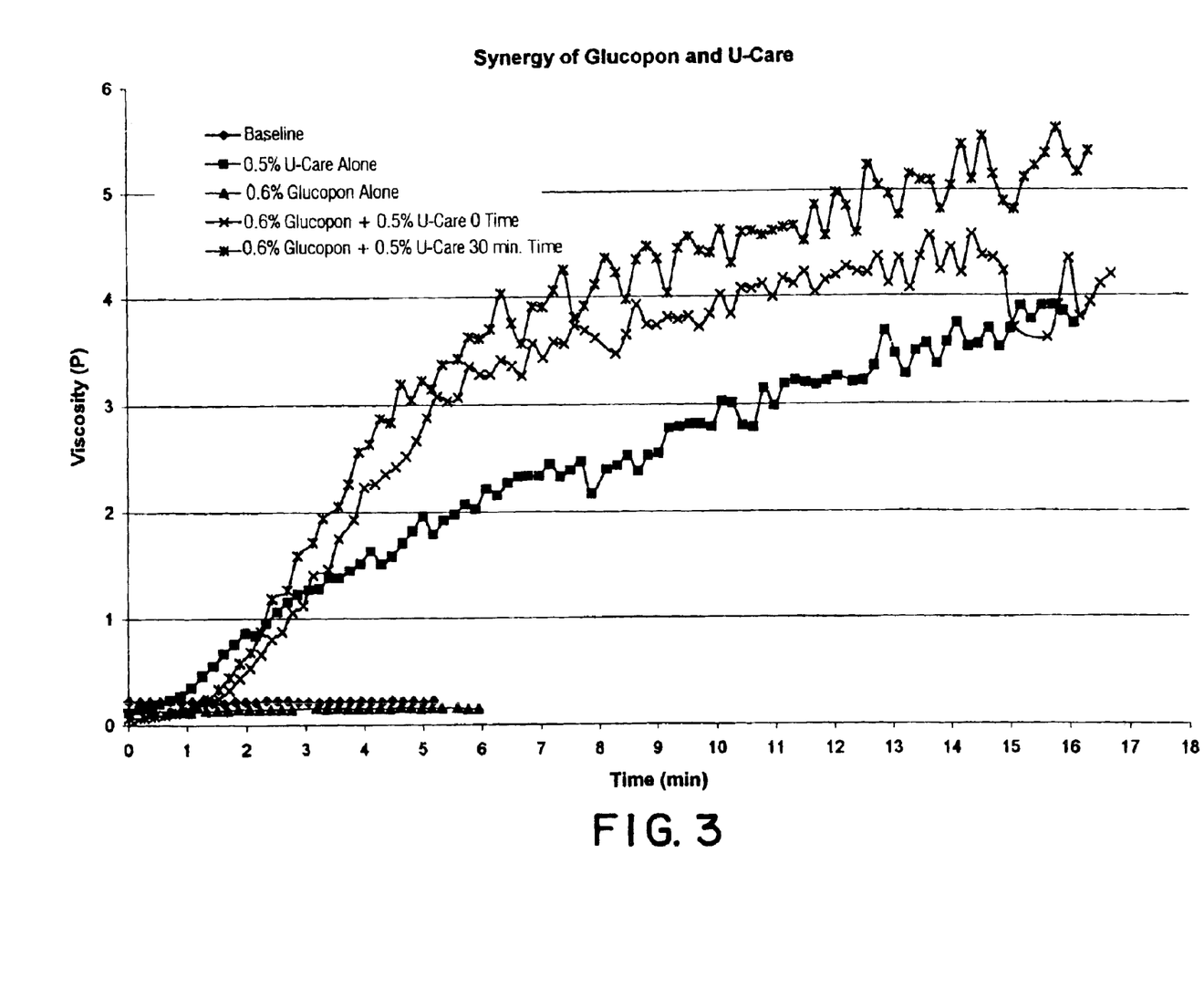
FIG. 3 is a graphical representation of the viscous component of complex viscosity as a function of time for the fluids tested in the Example herein.
Figure 4:
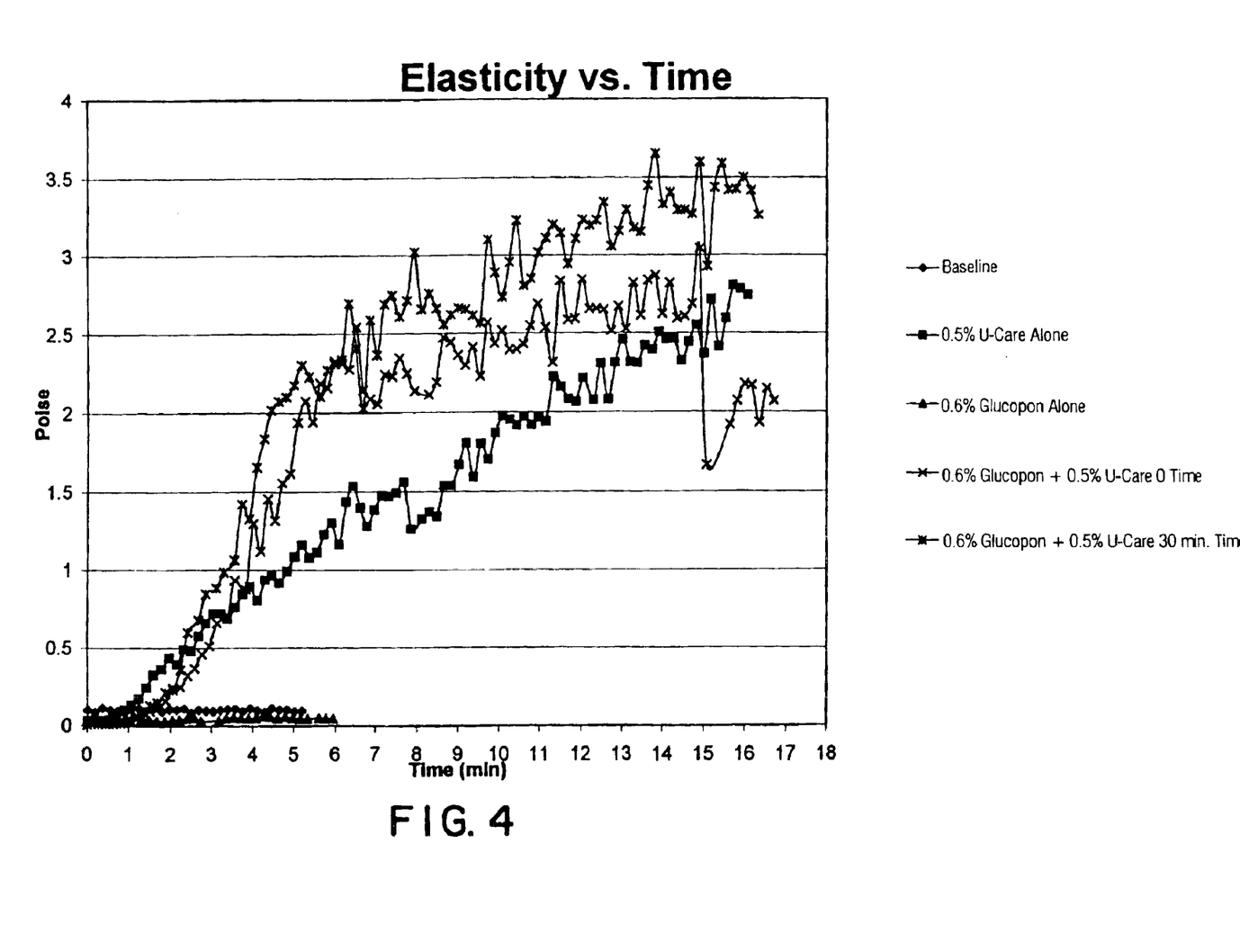
FIG. 4 is a graphical representation of the elastic component of complex viscosity as a function of time for the fluids tested in the Example herein.

The test was performed first on 0.5% UCARE™ alone added to the simulant, resulting in a viscosity of about 3.5 P after 15 minutes. The test was then performed on 0.5% UCARE™ and 0.6% GLUCOPON 220 together added to the simulant, resulting in a viscosity of about 4.5 P after 15 minutes. It was then found that by first adding 0.6% GLUCOPON to the simulant, then 30 minutes later adding 0.5% UCARE™, the viscosity was about 5.3 after 15 minutes, or 45 minutes from the time GLUCOPON and the simulant were combined. The data from these tests are graphically represented in FIGS. 3 and 4, with the rate of gelling represented by the slope of the curve which also increased compared to UCARE™ alone.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An absorbent material component comprising:
    a layer of absorbent material;
    a red blood cell lysing agent applied to a central region of the layer; and
    a gelling agent applied to a peripheral region of the layer;
    wherein the red blood coil lysing agent and the gelling agent are applied separately and not integrated together into the absorbent material component.

2. The absorbent material of claim 1 wherein the layer of absorbent material comprises a material selected from the group consisting of airlaid, airformed, wetlaid, absorbent laminates, nonwovens, fluid permeable polymeric film, and combinations thereof.

3. The absorbent material of claim 2, wherein the layer of absorbent material further comprises a superabsorbent material.

4. The absorbent material of claim 1, wherein the gelling agent is selected from the group consisting of chitosan salts, polyquaternium cellulosic polymer, and cellulose with propylene oxide groups.

5. The absorbent material of claim 1 wherein the red blood cell lysing agent is selected from the group consisting of an octylpolyglycoside, an alkoxylated polysiloxane, an alkoxylated alcohol, an alkyl substituted amino acid, an alkyl sulfate, a aulfosuccinate, a sarcosinate, saponin, and combinations thereof.

6. The absorbent material of claim 1, wherein the gelling agent is present in a concentration of between about 1% and about 15% by weight of the material.

7. The absorbent material of claim 1, wherein the gelling agent is present in a concentration of between about 2% and about 10% by weight of the material.

8. The absorbent material of claim 1, wherein the gelling agent is present in a concentration of between about 3% and about 8% by weight of the material.

9. The absorbent material of claim 1, wherein the red blood cell lysing agent is present in a concentration of between about 2% and about 40% by weight of the material.

10. The absorbent material of claim 1, wherein the red bleed cell lysing agent is present in a concentration of between about 6% amid about 35% by weight of the material.

11. The absorbent material of claim 1, wherein the red blood cell lysing agent is present in a concentration of between about 8% and about 30% by weight of the material.

12. An absorbent laminate comprising,
a central region of a first layer of absorbent material treated with a red blood cell lysing agent; and
a peripheral region of a second layer of absorbent material treated with a gelling agent, wherein the central region of the first layer is not treated with the gelling agent and the peripheral region of the second layer is not treated with the red blood cell lysing agent.

13. The absorbent laminate of claim 12, wherein the first layer comprises a liner and the second layer comprises a containment layer.

14. The absorbent laminate of claim 12, wherein the first layer comprises an intake layer adjacent a liner, and the second layer comprises a containment layer adjacent the intake layer.

15. The absorbent laminate of claim 12, wherein the first layer comprises a material selected from the group consisting of airlaid, airformed, wetlaid, absorbent laminates, nonwovens, fluid permeable polymeric film, and combinations thereof.

16. The absorbent laminate of claim 12, wherein the second layer comprises a material selected from the group a insisting of airlaid, airformed, wetlaid, absorbent laminates, nonwovens and combinations thereof.

17. The absorbent laminate of claim 16, wherein the second layer further comprises a superabsorbent material.

18. The absorbent laminate of claim 12, wherein the gelling agent is selected from the group consisting of chitosan salts, polyquaternium cellulosic polymer, and cellulose with propylene oxide groups.

19. The absorbent laminate of claim 12, wherein the red blood cell lysing agent is selected from the group consisting of an octylpolyglycoside, an alkoxylated polysiloxane, an alkoxylated alcohol, an alkyl-substituted amino acid, an alkyl sulfate, a sulfosuccinate, a sarcosinate, saponin, and combinations thereof.

20. The absorbent laminate of claim 12, wherein the gelling agent is present in a concentration of between about 1% and about 15% by weight of the laminate.

21. The absorbent laminate of claim 12, wherein the gelling agent is present in a concentration of between about 2% and about 10% by weight of the laminate.

22. The absorbent laminate of claim 12, wherein the gelling agent is present in a concentration of between about 3% and about 8% by weight of the laminate.

23. The absorbent laminate of claim 12, wherein the red blood cell lysing agent is present in a concentration of between about 2% and about 40% by weight of the laminate.

24. The absorbent laminate of claim 12, wherein the red blood cell lysing agent is present in a concentration of between about 6% and about 35% by weight of the laminate.

25. The absorbent laminate of claim 12, wherein the red blood cell lysing agent is present in a concentration of between about 8% and about 30% by weight of the laminate.

* * * * *

UNITED STATES PATENT AND TRADEMARK OFFICE
CERTIFICATE OF CORRECTION

PATENT NO. : 6,867,344 B2
DATED : March 15, 2005
INVENTOR(S) : David Charles Potts et al.

It is certified that error appears in the above-identified patent and that said Letters Patent is hereby corrected as shown below:

Column 10,
Line 38, replace "coil" with -- cell --
Line 57, replace "aulfosuccinate" with -- sulfosuccinate --.

Column 11,
Line 5, replace "bleed" with -- blood --;
Line 6, replace "amid" with -- and --;
Line 32, delete the second occurrence of "a";
Line 33, replace "insisting" with -- consisting --.

Signed and Sealed this

Thirty-first Day of May, 2005

JON W. DUDAS
*Director of the United States Patent and Trademark Office*